United States Patent [19]

Higgins, Jr. et al.

[11] 3,959,395

[45] May 25, 1976

[54] RECOVERY OF POLYMERIZATION INHIBITOR

[75] Inventors: Thomas D. Higgins, Jr., Texas City; Raymond A. Newsom, Dickinson, both of Tex.

[73] Assignee: Monsanto Company, St. Louis, Mo.

[22] Filed: Dec. 26, 1974

[21] Appl. No.: 536,271

[52] U.S. Cl. .................. 260/622 R; 260/621 A; 260/627 R; 260/669 A
[51] Int. Cl.$^2$ .................. C07C 79/24; C07C 37/28
[58] Field of Search ........ 260/622 R, 627 R, 621 H, 260/621 A, 624 A, 621 B, 669 A; 208/251 R, 252, 263; 203/9

[56] References Cited
UNITED STATES PATENTS 3,335,185   8/1967   Dykes ........................ 260/622 R Primary Examiner—James O. Thomas, Jr.
Assistant Examiner—W. B. Lone
Attorney, Agent, or Firm—Elizabeth F. Sporar

[57] ABSTRACT

A process is provided for recovery and re-use of dinitrophenols employed as inhibitors of polymerization in the distillation and purification of styrene. The styrene still residues commonly referred to as tar or tars are treated with an aqueous hydroxide at a controlled pH, the phases are separated, the aqueous phase is treated with an acid and an organic solvent at a controlled pH and the resulting organic phase is recycled to a suitable point in the styrene purification system. The recycled solution is a more effective inhibitor than the dinitrophenol originally employed.

5 Claims, No Drawings

RECOVERY OF POLYMERIZATION INHIBITOR

BACKGROUND OF THE INVENTION

The present invention relates to inhibition of polymerization of monomeric aromatic compounds during the distillation thereof. More particularly, it relates to recovery and re-use of dinitrophenol compounds employed to inhibit the polymerization of styrene during distillation.

Vinyl aromatic compounds, such as styrene, its homologs and analogs, tend to polymerize upon standing at ordinary temperatures and particularly when subjected to elevated temperatures. Concentration and purification of these monomers is ordinarily effected by distillation or fractionation and in these operations considerable difficulty can be encountered due to polymer formation. The polymer can be deposited upon the surfaces of the equipment and accumulate to the extent that the distillation must be interrupted at frequent intervals to clean out the equipment. In addition to the fact that this would result in substantial losses of the monomer, the delays in production caused by the necessity of removing the polymer formed could also be an important cost factor. It is, accordingly, essential to prevent premature polymerization and in common practice this is done by employing a polymerization inhibitor during processing of monomers such as styrene by distillation and fractionation.

A large number of chemical compounds are known to be effective for use as polymerization inhibitors for vinyl aromatic compounds and, in particular, for styrene. In their book "Styrene, Its Polymers, Copolymers and Derivatives," Part I, p. 262, Boundy and Boyer disclose that ortho-nitrophenols are very good retarders of polymerization at elevated temperatures. S. G. Foord, *J. Chem. Soc.*, 1940 pt. 1, 48-56, in a study of a large number of polymerization inhibitors tested with styrene reports that one nitro group in an aromatic compound gives strong retardation of polymerization, two nitro groups have a stronger inhibiting effect and three nitro groups an even stronger effect. Thus, the use of dinitrophenols to prevent polymerizaton of styrene during distillation is well known in the art.

In the course of processing or purifying styrene using such inhibitors, certain amounts of the inhibitor normally accumulate in the still residues of the product styrene column which are commonly referred to as styrene tar or tars and are disposed of as waste, usually by burning. The phenolic compounds are, however, sufficiently expensive to justify their recovery for re-use. It is accordingly an object of the present invention to provide a process for recovery of dinitrophenol inhibitors used in styrene distillation in a form suitable for re-use in the styrene purification system. In fact, the recovery method of the present invention provides a solution of dinitrophenol inhibitors which is more effective than the commercial dinitrophenols ordinarily employed in retarding polymerization during the distillation of styrene. Other objects and advantages of the invention will become apparent from the following description thereof.

SUMMARY OF THE INVENTION

According to the invention, a process is provided for recovery and re-use of dinitrophenol inhibitors from styrene tar which comprises the steps of: (1) intimately contacting styrene tar containing dinitrophenol inhibitor with an aqueous solution of the hydroxide of an alkali metal or ammonia while controlling the pH of the aqueous phase between 5 and 10, (2) separating the resulting phases, (3) intimately contacting the separated aqueous phase simultaneously with a mineral acid and an organic solvent while controlling the aqueous phase at a pH below 3, (4) recovering the organic phase containing substantially all the dinitrophenol dissolved therein and (5) recycling said organic phase to a suitable point in the styrene distillation or purification system. In the preferred embodiment of the invention, the organic solvent employed in Step 3 is either ethylbenzene or a so-called "dehydrogenated mixture" which for the purposes of this specification and claims is defined as the mixture obtained when ethylbenzene is subjected to dehydrogenation to produce styrene which consists essentially of a mixture of styrene, ethylbenzene, toluene and benzene. The use of this particular solvent provides a recovered solution of the dinitrophenol inhibitor which can be directly recycled to any one of several points in a styrene purification system without the introduction of extraneous materials into the system.

In another embodiment of the invention, ammonia gas can be employed for treating the styrene tar in the recovery process of the present invention instead of aqueous ammonium hydroxide. In this mode of operation, the dinitrophenols in the tar will be precipitated as solid salts which can be separated from the mixture by conventional techniques of filtration, centrifuging, etc. For re-use, the precipitated salts would then be acidified and taken up in an organic solvent such as dehydrogenated mixture or ethylbenzene. The operations involved using this method are somewhat more difficult from the standpoint of materials handling and so the method employing aqueous treating agents is the preferred one.

DESCRIPTION OF PREFERRED EMBODIMENT

In the first step of the process styrene tar containing small amounts of a dinitrophenol inhibitor is contacted with an aqueous alkaline solution. Aqueous solutions suitable for use are those of sodium hydroxide, potassium hydroxide, lithium hydroxide and the like or ammonium hydroxide. Preferred for use is sodium hydroxide. The concentration of the solution employed is that required to provide a ratio of $H_2O$/tar by volume anywhere in the range from 1:10 to 10:1. Preferably, the water/tar ratio is maintained from about 1:1 to about 1:3. Although the pH in this step may be controlled in the range from 5 to 10, a pH range between 7 and 9 is preferred. The temperature at which contacting is effected is not critical and may be anywhere from room temperature (25° C) to about 100° C. Preferably, temperatures from about 70° to about 95° C are employed since phase separation is facilitated at these temperatures.

The separation of the two phases in Step 2 can be effected in any conventional manner such as by settling and decanting the upper tar layer and drawing off the aqueous layer, centrifuging the mixture, etc. The separated tar can, if desired, be employed as fuel or used for other suitable purposes.

In the treatment of the aqueous phase in Step 3, it is important that the acid and organic solvent be added simultaneously. Otherwise problems stemming from precipitation are encountered. Mineral acids such as HCl, $H_2SO_4$, $H_3PO_4$ and the like can be used with $H_2SO_4$ being preferred. The amount of acid added is such as to maintain the pH of the aqueous phase <3 and preferably <1.

The organic solvent employed in Step 3 can be any solvent which will dissolve dinitrophenols and which is compatible in the styrene distillation or purification system. However, the process is most satisfactory and efficient as explained above when ethylbenzene or dehydrogenated mixture is employed as the solvent in this step. The volume ratio of solvent employed to aqueous phase being treated is from about 1:10 to 10:1 and preferably the solvent/aqueous phase volume ratio is from about 3:1 to about 1:1. The temperature at which Step 3 is conducted is not critical. Preferred operation is at low temperatures, i.e., below 60° C, since these result in reduced quantities of dinitrophenols remaining in the waste water.

After separation of the organic aqueous phases from Step 3 and prior to recycle of the organic phase, the organic phase may be washed with water one or more times and dried to remove any residual traces of acid. The wash water can then be used as make-up in diluting the concentrated alkali to the desired concentration for use in Step 1.

The process which can be operated on either a continuous or batch basis is illustrated in the following examples which, however, are not to be construed as limiting it in any manner except as it is limited in the attached claims.

EXAMPLE 1

A one-liter, round-bottomed flask provided with two inlets, baffles installed to provide thorough agitation and an overflow outlet was employed as a contact vessel. Styrene tar obtained as a bottoms stream from a styrene recovery distillation column operated in a commercial plant and containing 1.63% by weight of dinitrophenol was continuously fed at a rate of 39.3 grams per minute to the contactor as 1.25% Aqueous sodium hydroxide was also charged continuously at a rate of 11.2 grams per minute. The temperature of the contactor was maintained at 87° to 89° C and the pH of the aqueous phase was about 8.2.

The effluent stream from the contactor continuously overflowed into a separator where the top tar layer was continuously decanted. The water phase was pumped continuously into a second contactor similar to the first together with 37.7 grams per minute of a dehydrogenated mixture consisting of styrene, ethylbenzene, toluene and benzene to which 18% HCl was introduced simultaneously and continuously at a rate of 1.5 grams per minute. Temperature of the mixture during agitation in the second contactor was about 35° C and the pH of the aqueous phase in the second contactor was 1.1. The mixture continuously overflowed into a second separator, the organic layer being continuously removed and the aqueous layer being continuously pumped to waste facilities. The waste water discharged from the system contained 0.014% dinitrophenol while the organic layer contained 1.6% dinitrophenol. This represents a 95.6% recovery of dinitrophenol. The organic layer constitutes a suitable solution of the dinitrophenol for employment directly as an inhibitor in the distillation of a dehydrogenated mixture of ethylbenzene for recovery of styrene therefrom.

EXAMPLE 2

Styrene tar (213.3g) containing 3.84% 2,4-dinitrophenol (8.20g) was introduced into a 500-ml Erlenmeyer flask equipped with a stirrer and disposed on a hot plate. To the flask was added 80 ml of 2.5% aqueous NaOH with heating and vigorous stirring. The temperature was brought up to 90° C with the stirred mixture having a pH of 8.1. The hot mixture was poured into a heated separatory funnel and permitted to separate into two liquid phases.

The water layer (bottom) was drawn off and introduced into a 500-ml Erlenmeyer flask. About 190 ml of the dehydrogenated mixture defined above was added to the flask while 13.1g of 18% HCl was slowly and simultaneously introduced into the flask to adjust the pH of the stirred mixture to about 1.5. The contents of the flask were transferred to a separatory funnel where the mixture was allowed to settle into two liquid phases. The water phase was drawn off and discarded. The solvent layer weighed 179.2g and upon analysis was found to contain 4.45% 2,4-dinitrophenol representing a recovery of this inhibitor material of 97.2%.

EXAMPLE 3

A mixture resulting from the dehydrogenation of ethylbenzene consisting of styrene, toluene, benzene and unreacted ethylbenzene and containing technical-grade 2,4-dinitrophenol in an amount of about 2090 parts by weight per million parts of the contained styrene was fed continuously to a laboratory distillation column capable of separating ethylbenzene from styrene to produce a styrene fraction containing a minimum of 99.6% styrene (on polymer-free basis). The column was operated at an overhead pressure of 414 mm Hg which resulted in a bottoms temperature of approximately 131° C. The level in the column sump was maintained so as to provide an average styrene residence time in the column of 60 minutes. After allowing the system to equilibrate, samples of the column bottoms were collected for determination of their polymer content.

Polymer determinations were made by evaporation of the samples at approximately 1 mm Hg pressure and 50° C and weighing of the residues to constant weight. Residues of the feed material were determined in the same manner and corrected for styrene content. Net polymer make determined by difference was 0.67 polymer/100g of styrene produced.

The above run was repeated except that the 2,4-dinitrophenol added to the dehydrogenated mixture was dinitrophenol recovered from styrene tar, i.e., the solution of dinitrophenol obtained from the operation of a continuous recovery system such as is described in Example 1. The mixture fed to the distillation column contained about 2060 ppm of the dinitrophenol based on contained styrene. Temperature, pressure and residence time in the distillation were the same as in the previous run. The net polymer make determined in the same manner was 0.52g polymer/100 g of styrene produced, a decrease of more than 20% over that obtained in the run with the technical-grade dinitrophenol.

What is claimed is:

1. The process for recovery of dinitrophenol inhibitors from styrene tar which comprises the steps of:
    1. intimately contacting styrene tar containing dinitrophenol inhibitor at a temperature between about 70° and about 95°C with an aqueous solution of the hydroxide of an alkali metal or ammonia while controlling the pH of the aqueous phase between about 5 and 10,
2. separating the resulting liquid phases,
3. intimately contacting the separated aqueous phase simultaneously with a mineral acid and an organic solvent for dinitrophenol selected from the group consisting of ethylbenzene and mixtures of ethylbenzene, styrene, toluene and benzene while controlling the pH of the aqueous phase below 3, and
4. recovering the organic phase containing substantially all the dinitrophenol dissolved therein.

2. The process of claim 1 wherein said mineral acid is hydrochloric acid.

3. The process of claim 2 wherein said hydroxide is sodium hydroxide.

4. The process of claim 3 wherein the pH of the aqueous phase in Step 1 is controlled between 7 and 9.

5. The process of claim 4 wherein the pH of the aqueous phase in Step 3 is controlled below 1.

* * * * *